US011173185B2

(12) United States Patent
Furuichi et al.

(10) Patent No.: US 11,173,185 B2
(45) Date of Patent: Nov. 16, 2021

(54) METHOD FOR PRODUCING CULTURE PRODUCT OF *LACTOBACILLUS PLANTARUM*

(71) Applicant: MEIJI CO., LTD., Tokyo (JP)

(72) Inventors: Keisuke Furuichi, Kanagawa (JP); Takayuki Toshimitsu, Kanagawa (JP); Satoru Ozaki, Kanagawa (JP)

(73) Assignee: MEIJI CO., LTD., Tokyo (JP)

( * ) Notice: Subject to any disclaimer, the term of this patent is extended or adjusted under 35 U.S.C. 154(b) by 69 days.

(21) Appl. No.: 16/325,820

(22) PCT Filed: Aug. 18, 2017

(86) PCT No.: PCT/JP2017/029585
§ 371 (c)(1),
(2) Date: Feb. 15, 2019

(87) PCT Pub. No.: WO2018/038004
PCT Pub. Date: Mar. 1, 2018

(65) Prior Publication Data
US 2020/0016221 A1    Jan. 16, 2020

(30) Foreign Application Priority Data

Aug. 22, 2016 (JP) .............................. JP2016-162010

(51) Int. Cl.
*A61K 35/747* (2015.01)
*A23L 33/135* (2016.01)
(Continued)

(52) U.S. Cl.
CPC .......... *A61K 35/747* (2013.01); *A23L 33/135* (2016.08); *C12N 1/20* (2013.01); *C12N 1/38* (2013.01); *C12Q 1/02* (2013.01)

(58) Field of Classification Search
CPC ....... A61K 35/747; A23L 33/135; C12N 1/20; C12N 1/38; C12Q 1/02; G01N 2333/335; A61P 37/06; A61P 29/00
See application file for complete search history.

(56) References Cited

U.S. PATENT DOCUMENTS 9,340,588 B2 *  5/2016  Sanchez Garcia ...... A23L 33/18
2011/0217402 A1  9/2011  van Tol et al.

FOREIGN PATENT DOCUMENTS

JP    2007-089497 A    4/2007
JP    2008-031153 A    2/2008
(Continued)

OTHER PUBLICATIONS

Chemistrystore.com. 2015. Polysorbate 80. Retrieved from: https://www.chemistrystore.com/Soap_Making_Supplies-Polysorbate_80.html. (Year: 2015).*

(Continued)

*Primary Examiner* — David W Berke-Schlessel
(74) *Attorney, Agent, or Firm* — Posz Law Group, PLC

(57) ABSTRACT

Provided is a method of producing a culture product of a microorganism, for obtaining a culture product excellent in anti-inflammatory property in which a ratio between the production amounts of IL-10 and IL-12 (ratio of IL-10/IL-12) is large. Specifically, provided is a method of producing a culture product of *Lactobacillus plantarum*, including culturing *Lactobacillus plantarum* using a medium containing an unsaturated fatty acid ester until a time point at or before an end of a logarithmic growth phase, to thereby obtain a culture product of *Lactobacillus plantarum*. The unsaturated fatty acid ester is an ester formed through a reaction between a monovalent or polyvalent unsaturated (Continued)

fatty acid and a polyhydric alcohol, or a derivative of the ester. A preferred example of the unsaturated fatty acid ester is a monooleic acid ester.

15 Claims, 6 Drawing Sheets

(51) Int. Cl.
    *C12N 1/38* (2006.01)
    *C12N 1/20* (2006.01)
    *C12Q 1/02* (2006.01)

(56) References Cited

FOREIGN PATENT DOCUMENTS

JP         2011-250756 A    12/2011
JP            4979689 B2     7/2012

OTHER PUBLICATIONS

Kankaanpaa et al. 2004. Effects of Polyunsaturated Fatty Acids in Growth Medium on Lipid Composition and on Physicochemical Surface Properties of Lactobacilli. 70(1): 129-136. (Year: 2004).*
Sigma. Tween 80: Product Information. Retrieved from: file:///C:/Users/khunter1/Documents/e-Red%20Folder/16325820/Sigma%20Tween%2080.pdf.*
Todar, K. 2015. The Growth of Bacterial Populations. Todar's Online Textbook of Bacteriology. Retrieved from: http://textbookofbacteriology.net/growth_3.html (Year: 2015).*
Todorov, Svetoslav Dimitrov; et al; "Effect of Growth Medium on Bacteriocin Production by Lactobacillus plantarum ST194BZ, a Strain Isolated from Boza" Food Technology and Biotechnolgy, 43, 165-173, 2005 (Year: 2005).*
International Search Report of the International Searching Authority dated Sep. 19, 2017 for the corresponding international application No. PCT/JP2017/029585 (and English translation).
Written Opinion of the International Searching Authority dated Sep. 19, 2017 for the corresponding international application No. PCT/JP2017/029585 (and English translation).
Liam O'Mahony et al., "Lactobacillus and Bifidobacterium in Irritable Bowel Syndrome: Symptom Responses and Relationship to Cytokine Profiles." Gastroenterology vol. 128, Mar. 2005, pp. 541-551 (discussed on p. 1 of the specification).
Harry Sokol et al., "Faecalibacterium prausnitzii is an anti-inflammatory commensal bacterium identified by gut microbiota analysis of Crohn disease patients." Proc. Natl. Acad. Sci. USA, vol. 105; 2008; pp. 16731-16736 (discussed on p. 1 of the specification).
Yang Yu et al., "Central Gene Transfer of Interleukin-10 Reduces Hypothalamic Inflammation and Evidence of Heart Failure in Rats After Myocardial Infarction." Circulation Research vol. 101, Aug. 3, 2007; pp. 304-312 (discussed on p. 1 of the specification).
Saskia Van Hemert et al., "Identification of Lactobacillus plantarum genes modulating the cytokine response of human peripheral blood mononuclear cells." BMC Microbiology vol. 10, No. 293, 2010, pp. 1-13 (discussed on p. 4 of the specification and cited in the PCT Search Report).

Peter Van Baarlen et al., "Differential NF-kB pathways induction by Lactobacillus plantarum in the duodenum of healthy humans correlating with immune tolerance." Proc. Natl. Acad. Sci. USA, vol. 106, No. 7; Feb. 17, 2009; pp. 2371-2376 (discussed on p. 4 of the specification).
T. Toshimitsu et al. "Effects of Lactobacillus plantarum Strain OLL2712 Culture Conditions on the Anti-inflammatory Activities for Murine Immune Cells and Obese and Type 2 Diabetic Mice." Applied and Environmental Microbiology, vol. 83, No. 7; Apr. 2017; pp. 1-11 (cited in the PCT Search Report).
Search Report dated Apr. 10, 2020 for the corresponding SG application No. 11201901406Q (English translation).
Written Opinion dated Apr. 10, 2020 for the corresponding SG application No. 11201901406Q (English translation).
Fujii, T. et al., Two Homologous Agr-Like Quorum-Sensing Systems Cooperatively Control Adherence, Cell Morphology, and Cell Viability Properties in Lactobacillus plantarum WCFS1. Journal of Bacteriology, Sep. 19, 2008, vol. 190, No. 23, pp. 7655-7665.
Toshimitsu, T., Identification of a Lactobacillus plantarum strain that ameliorates chronic inflammation and metabolic disorders in obese and type 2 diabetic mice. Journal of Dairy Science, Dec. 2015, vol. 99, No. 2, pp. 933-946.
Johnsson, J. et al., Cellular Fatty Acid Profiles of Lactobacillus and Lactococcus Strains in Relation to the Oleic Acid Content of the Cultivation Medium. Applied and Environmental Microbiology, Dec. 1995, vol. 61, No. 12, pp. 4497-4499.
Manirarora, J.N. et al., NOD Dendritic Cells Stimulated with Lactobacilli Preferentially Produce IL-10 versus IL-12 and Decrease Diabetes Incidence. Clinical and Developmental Immunology, Jun. 12, 2011, vol. 2011, pp. 1-12.
De Man, J.C. et al., A medium for the cultivation of Lactobacilli. Journal of Applied Bacteriology, Apr. 1960, vol. 23, No. 1, pp. 130-135.
Toshimitsu, T. et al., Effects of Lactobacillus plantarum Strain OLL2712 Culture Conditions on the Anti-inflammatory Activities for Murine Immune Cells and Obese and Type 2 Diabetic Mice. Applied and Environmental Microbiology, Mar. 17, 2017, vol. 83, No. 7, pp. e03001-e03116.
Corcoran, B.M. et al., Growth of probiotic lactobacilli in the presence of oleic acid enhances subsequent survival in gastric juice. Microbiology, Jan. 1, 2007, vol. 153, No. 1, pp. 291-299.
Vinderola, G. et al., Effects of the oral administration of the exopolysaccharide produced by Lactobacillus kefiranofaciens on the gut mucosal immunity. Cytokine, Jan. 2007, vol. 36, No. 5-6, pp. 254-260 (abstract only).
Van Baarlen, P. et al.,"Differential NF-kB pathways induction by *Lactobacillus plantarum* in the duodenum of healthy humans correlating with immune tolerance" PNAS, Feb. 17, 2009, vol. 106, No. 7, pp. 2371-2376.
Veerkamp, J.H.,"Fatty Acid Composition of *Bifidobacterium* and *Lactobacillus* Strains" Journal of Bacteriology, Nov. 1971, vol. 108, No. 2, pp. 861-867, American Society for Microbiology.
Toshimitsu, T. et al.,"Identification of a *Lactobacillus plantarum* strain that ameliorates chronic inflammation and metabolic disorders in obese and type 2 diabetic mice" J. Daily Sci., (Feb. 2016), vol. 99, pp. 933-946, American Dairy Science Association.

\* cited by examiner

METHOD FOR PRODUCING CULTURE PRODUCT OF *LACTOBACILLUS PLANTARUM*

CROSS REFERENCE TO RELATED APPLICATIONS

The present disclosure is a U.S. national stage application of PCT/JP2017/029585 filed on Aug. 18, 2017, and is based on Japanese Patent Application No. 2016-162010 filed on Aug. 22, 2016, the disclosures of which are incorporated herein by reference.

TECHNICAL FIELD

The present invention relates to a method of producing a culture product of *Lactobacillus plantarum*.

BACKGROUND ART

Interleukin (IL)-10 is an anti-inflammatory cytokine produced by immune cells (such as dendritic cells or macrophages), and plays an important role in reducing excessive inflammation in a living body. That is, when production of IL-10 is induced, a disease or the like resulting from inflammation can be ameliorated. For example, there is a report that administration of lactic acid bacteria having high production-inducing activity of IL-10 reduces intestinal inflammation (see Non-Patent Literatures 1 and 2). In addition, there is a report that transgenic overexpression of IL-10 reduces myocardial infarction via reduction of inflammation (see Non-Patent Literature 3).

Meanwhile, interleukin (IL)-12 is similar to IL-10 in being a cytokine produced by immune cells, but different from IL-10 in exhibiting a function of promoting inflammation in a living body.

Therefore, like the production-inducing activity of IL-10, a ratio between production amounts of IL-10 and IL-12 (IL-10/IL-12 production amount ratio) is also regarded as an important indicator of anti-inflammatory activity. That is, when a strain (such as lactic acid bacteria) having high production-inducing activity of IL-10 and low production-inducing activity of IL-12 can be selected and used, a commercial product having high immunomodulatory activity (i.e. anti-inflammatory function) can be provided. Besides, as a result of the foregoing, in addition to the diseases such as intestinal inflammation and myocardial infarction, various diseases resulting from inflammation (such as metabolic syndrome, cancer, an autoimmune disease, and a neurodegenerative disease) can be expected to be ameliorated.

As a technology concerning the ratio between the production amounts of IL-10 and IL-12, in Patent Literature 1, there is described a method of producing an interleukin production regulator having an effect of maintaining or promoting production of interleukin-10 and an effect of maintaining or inhibiting production of interleukin-12, which contains a disrupted product of a microorganism belonging to the genus *Bifidobacterium* and is for use in prevention and/or treatment of an autoimmune disease or a gastrointestinal disease, wherein the method includes the steps of: disrupting the microorganism belonging to the genus *Bifidobacterium* by ultrasonication with an energy of 2,600 joules or more per ml of a sample; and removing an undisrupted product from the disrupted microorganism to prepare the disrupted product.

According to this method, a value of 10 or more can be obtained for the ratio between the production amounts of interleukin-10 and interleukin-12 (interleukin-10/interleukin-12 production amount ratio).

In addition, as an agent for promoting production of interleukin (IL)-10, in Patent Literature 2, there is described an interleukin 10 production promotor obtained by combining (A) a bacterium or yeast, or microorganism treated product free of an interleukin 12 production-inducing ability, and (B) a bacterium having an interleukin 12 production-inducing ability. In addition, in Patent Literature 2, as examples of the (A), there are described *Lactobacillus plantarum*, *Lactobacillus acidophilus*, *Bifidobacterium breve*, *Bifidobacterium bifidum*, and the like.

Incidentally, in ordinary cases, when the lactic acid bacteria or the like is cultured on a commercial scale and the resultant culture product is used as a raw material for a commercial product, culture conditions therefor are determined by considering the growth properties of the lactic acid bacteria or the like (i.e. the increase in density of bacterial cells). That is, in ordinary cases, composition and the like of a medium capable of increasing the density of the lactic acid bacteria or the like are chosen as culture conditions capable of maximizing the density of the bacterial cells of the lactic acid bacteria or the like, and with the use of such medium, the lactic acid bacteria or the like is cultured until a certain time point during a stationary phase past a logarithmic growth phase.

With regard to a culture period of the lactic acid bacteria or the like, for example, in Patent Literature 3, there is a description that, in a method of producing leaven, fermentation of bread dough-like dough is performed over a period until yeast and lactic acid bacteria reach an end of the stationary phase after undergoing the logarithmic growth phase.

Meanwhile, there are also known papers in which a comparison is made between a case in which culture is performed until the stationary phase and a case in which culture is performed until the logarithmic growth phase without reaching the stationary phase.

For example, in Non-Patent Literature 4, it is reported that, as compared to *L. plantarum* WCFS1 in the stationary phase, *L. plantarum* WCFS1 in the logarithmic growth phase strongly induces production of IL-10 in human-derived peripheral blood mononuclear cells (PBMC).

In addition, in Non-Patent Literature 5, it is reported that, when subjects (the number of subjects: eight) were administered *L. plantarum* WCFS1 in the logarithmic growth phase and the stationary phase, and expression of duodenal mucosal genes was comprehensively analyzed with microarrays, the *L. plantarum* WCFS1 in the stationary phase induced expression of genes involved in activation of NF-κB serving as an inflammation mediator, whereas the *L. plantarum* WCFS1 in the logarithmic growth phase induced expression of genes involved in anti-inflammatory property.

CITATION LIST

Patent Literature(s)

[Patent Literature 1] JP 4979689 B2
[Patent Literature 2] JP 2008-31153 A
[Patent Literature 3] JP 2007-89497 A

Non-Patent Literature(s)

[Non-Patent Literature 1] O'Mahony L, McCarthy J, Kelly P, Hurley G, Luo F, Chen K, O'Sullivan G C, Kiely B, Collins J K, Shanahan F, Quigley E M. 2005. *Lactobacillus* and *bifidobacterium* in irritable bowel syndrome: symptom responses and relationship to cytokine profiles. *Gastroenterology* 128:541-551.

[Non-Patent Literature 2] Sokol H, Pigneur B, Watterlot L, Lakhdari O, Bermúdez-Humarán L G, Gratadoux J J, Blugeon S, Bridonneau C, Furet J P, Corthier G, Grangette C, Vasquez N, Pochart P, Trugnan G, Thomas G, Blottière H M, Dore J, Marteau P, Seksik P, Langella P. 2008. *Faecalibacterium prausnitzii* is an anti-inflammatory commensal bacterium identified by gut microbiota analysis of Crohn disease patients. *Proc. Natl. Acad. Sci. USA* 105:16731-16736.

[Non-Patent Literature 3] Yu Y, Zhang Z H, Wei S G, Chu Y, Weiss R M, Heistad D D, Felder R B. 2007. Central gene transfer of interleukin-10 reduces hypothalamic inflammation and evidence of heart failure in rats after myocardial infarction. *Circ. Res.* 101:304-312.

[Non-Patent Literature 4] van Hemert S, Meijerink M, Molenaar D, Bron P A, de Vos P, Kleerebezem M, Wells J M and Marco M L. 2010. Identification of *Lactobacillus plantarum* genes modulating the cytokine response of human peripheral blood mononuclear cells. *BMC Microbiol.* 10:293.

[Non-Patent Literature 5] van Baarlen P, Troost F J, van Hemert S, van der Meer C, de Vos W M, de Groot P J, Hooiveld G J, Brummer R J and Kleerebezem M. 2008. Differential NF-kappaB pathways induction by *Lactobacillus plantarum* in the duodenum of healthy humans correlating with immune tolerance. *Proc. Natl. Acad. Sci. USA* 106:2371-2376.

SUMMARY OF INVENTION

Technical Problem

An object of the present invention is to provide a method of producing a culture product of a microorganism, for obtaining a culture product excellent in anti-inflammatory property in which a ratio between the production amounts of IL-10 and IL-12 (ratio of IL-10/IL-12) is large.

Solution to Problem

The inventors of the present invention have made extensive investigations in order to achieve the above-mentioned object, and as a result, have found that, when *Lactobacillus plantarum* is cultured using a medium containing an unsaturated fatty acid ester until a time point at or before the end of a logarithmic growth phase, to thereby obtain a culture product of *Lactobacillus plantarum*, a larger value is obtained for a ratio between the production amounts of IL-10 and IL-12 (production amount of IL-10/production amount of IL-12) in the obtained culture product as compared to a case in which the culture is performed until a stationary phase. Thus, the inventors have completed the present invention.

The present invention provides the following items [1] to [12].

[1] A method of producing a culture product of *Lactobacillus plantarum*, including culturing *Lactobacillus plantarum* using a medium containing an unsaturated fatty acid ester until a time point at or before an end of a logarithmic growth phase, to thereby obtain a culture product of *Lactobacillus plantarum*.

[2] The method of producing a culture product of *Lactobacillus plantarum* according to the above-mentioned item [1], wherein the end of the logarithmic growth phase is represented by a time point at which a bacterial count during culture of the *Lactobacillus plantarum* reaches a bacterial count that is half as large as a highest attainable bacterial count.

[3] The method of producing a culture product of *Lactobacillus plantarum* according to the above-mentioned item [1], wherein the end of the logarithmic growth phase is represented by a time point at which a consumption amount of a neutralizer to be used during neutral culture of the *Lactobacillus plantarum* reaches an amount that is half as large as a total consumption amount.

[4] The method of producing a culture product of *Lactobacillus plantarum* according to any one of the above-mentioned items [1] to [3], wherein the unsaturated fatty acid ester is an ester formed through a reaction between a monovalent or polyvalent unsaturated fatty acid and a polyhydric alcohol, or a derivative of the ester.

[5] The method of producing a culture product of *Lactobacillus plantarum* according to the above-mentioned item [4], wherein the monovalent or polyvalent unsaturated fatty acid is a monovalent to trivalent unsaturated fatty acid having 16 to 23 carbon atoms.

[6] The method of producing a culture product of *Lactobacillus plantarum* according to the above-mentioned item [4] or [5], wherein the unsaturated fatty acid ester is a monooleic acid ester.

[7] The method of producing a culture product of *Lactobacillus plantarum* according to the above-mentioned item [6], wherein the unsaturated fatty acid ester is a polyglycerol fatty acid ester, a sorbitan fatty acid ester, or a polysorbate.

[8] An anti-inflammatory agent, including, as an active ingredient, a culture product of *Lactobacillus plantarum* produced by the production method of any one of the above-mentioned items [1] to [7]. [9] A method of selecting a strain of *Lactobacillus plantarum*, including:

culturing each of a plurality of (i.e. two or more of) strains of *Lactobacillus plantarum* using a medium containing an unsaturated fatty acid ester until a time point at or before an end of a logarithmic growth phase, to thereby obtain a culture product of each of the strains;

subjecting the obtained culture product of each of the strains to an evaluation of production-inducing activity of interleukin-10; and selecting a strain having a large degree of an anti-inflammatory action from the plurality of strains based on a result of the evaluation.

[10] The method of selecting a strain of *Lactobacillus plantarum* according to the above-mentioned item [9], further including subjecting the obtained culture product of each of the strains to an evaluation of production-inducing activity of interleukin-12 in addition to the evaluation of production-inducing activity of interleukin-10, wherein selecting a strain (i.e. the selection of the strain) having a large degree of an anti-inflammatory action from the plurality of strains is performed based on results of the evaluations.

[11] The method of selecting a strain of *Lactobacillus plantarum* according to the above-mentioned item [9] or [10], wherein the end of the logarithmic growth phase is represented by a time point at which a bacterial count during culture of the *Lactobacillus plantarum* reaches a bacterial count that is half as large as a highest attainable bacterial count.

[12] The method of selecting a strain of *Lactobacillus plantarum* according to the above-mentioned item [9] or [10], wherein the end of the logarithmic growth phase is represented by a time point at which a consumption amount of a neutralizer to be used during neutral culture of the *Lactobacillus plantarum* reaches an amount that is half as large as a total consumption amount.

Advantageous Effects of Invention

According to the present invention, the culture product (i.e. the culture product of *Lactobacillus plantarum*) excellent in anti-inflammatory property in which the ratio between the production amounts of IL-10 and IL-12 (hereinafter sometimes referred to as "IL-10/IL-12 production amount ratio" or "IL-10/IL-12 production ratio") is large can be obtained.

DESCRIPTION OF EMBODIMENTS

Figure 1:
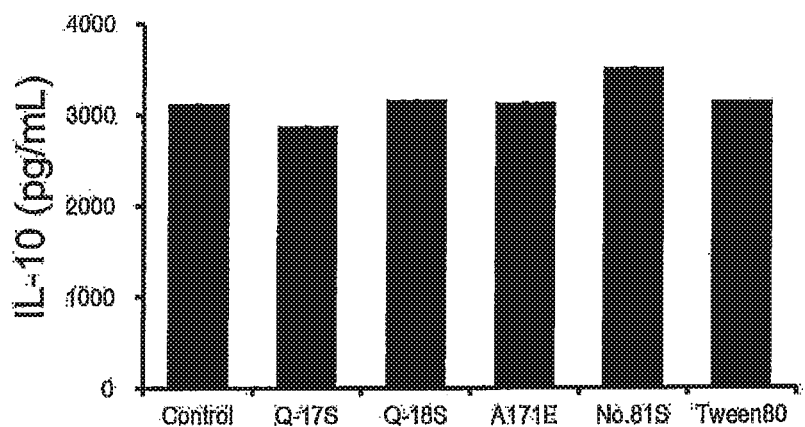
FIG. 1 is a graph for showing the production amounts of IL-10 in cases in which *Lactobacillus plantarum* OLL2712 is cultured using media containing unsaturated fatty acid esters (4 kinds), a medium containing a saturated fatty acid ester (for comparison; 1 kind), or a medium containing no unsaturated fatty acid ester and no saturated fatty acid ester (for a control; 1 kind).
Figure 2:
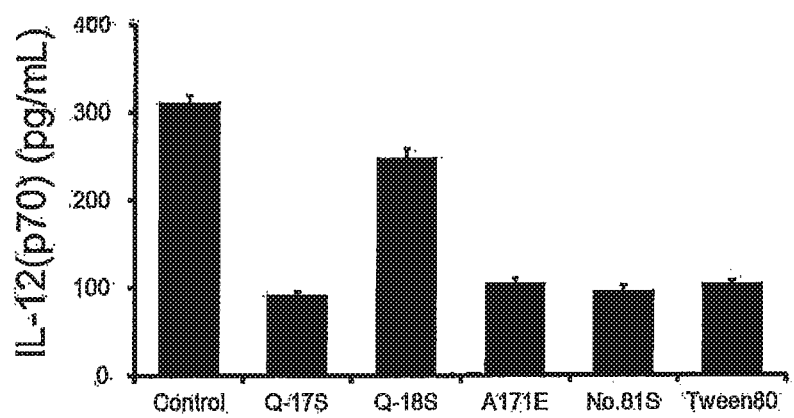
FIG. 2 is a graph for showing the production amounts of IL-12 in the culture shown in FIG. 1.
Figure 3:
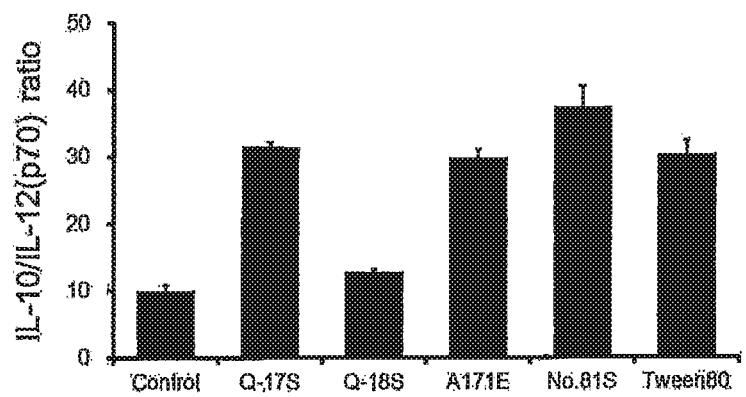
FIG. 3 is a graph for showing IL-10/IL-12 production amount ratios in the culture shown in FIG. 1.
Figure 4:
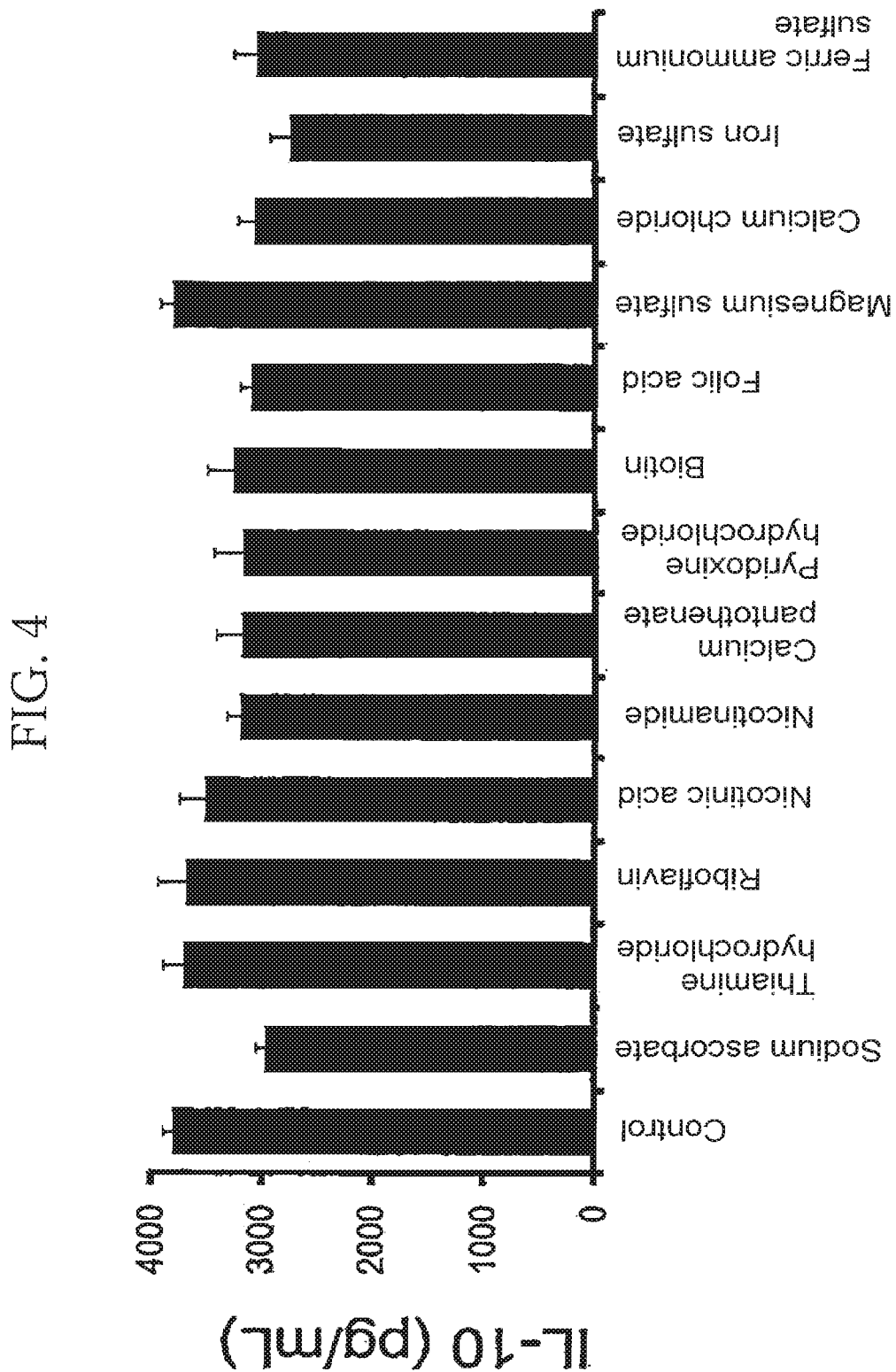
FIG. 4 is a graph for showing the production amounts of IL-10 in cases in which *Lactobacillus plantarum* OLL2712 is cultured using media containing substances other than unsaturated fatty acid esters (such as sodium ascorbate; 13 kinds) or a medium containing none of the substances (for a control; 1 kind).
Figure 5:
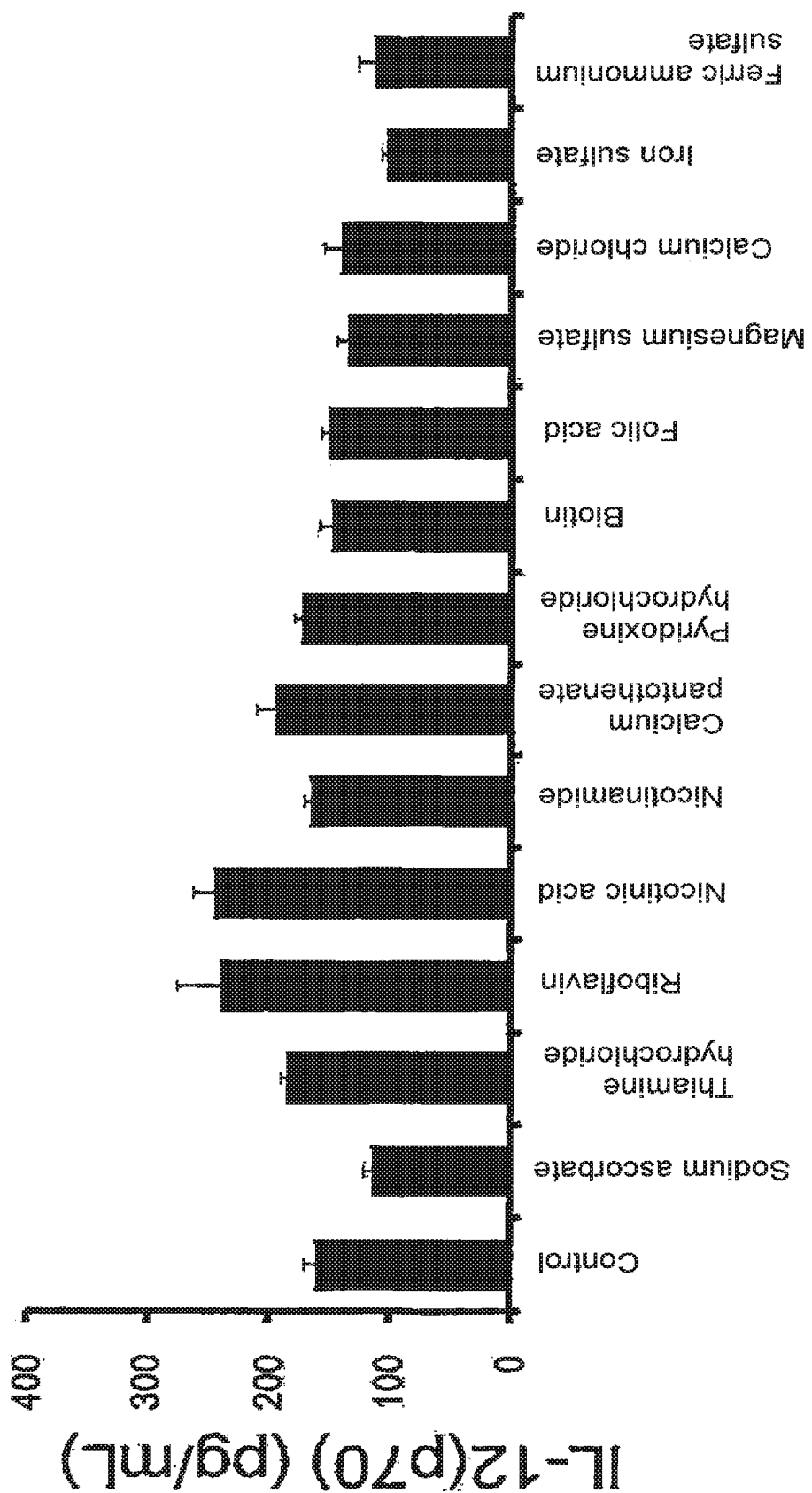
FIG. 5 is a graph for showing the production amounts of IL-12 in the culture shown in FIG. 4.
Figure 6:
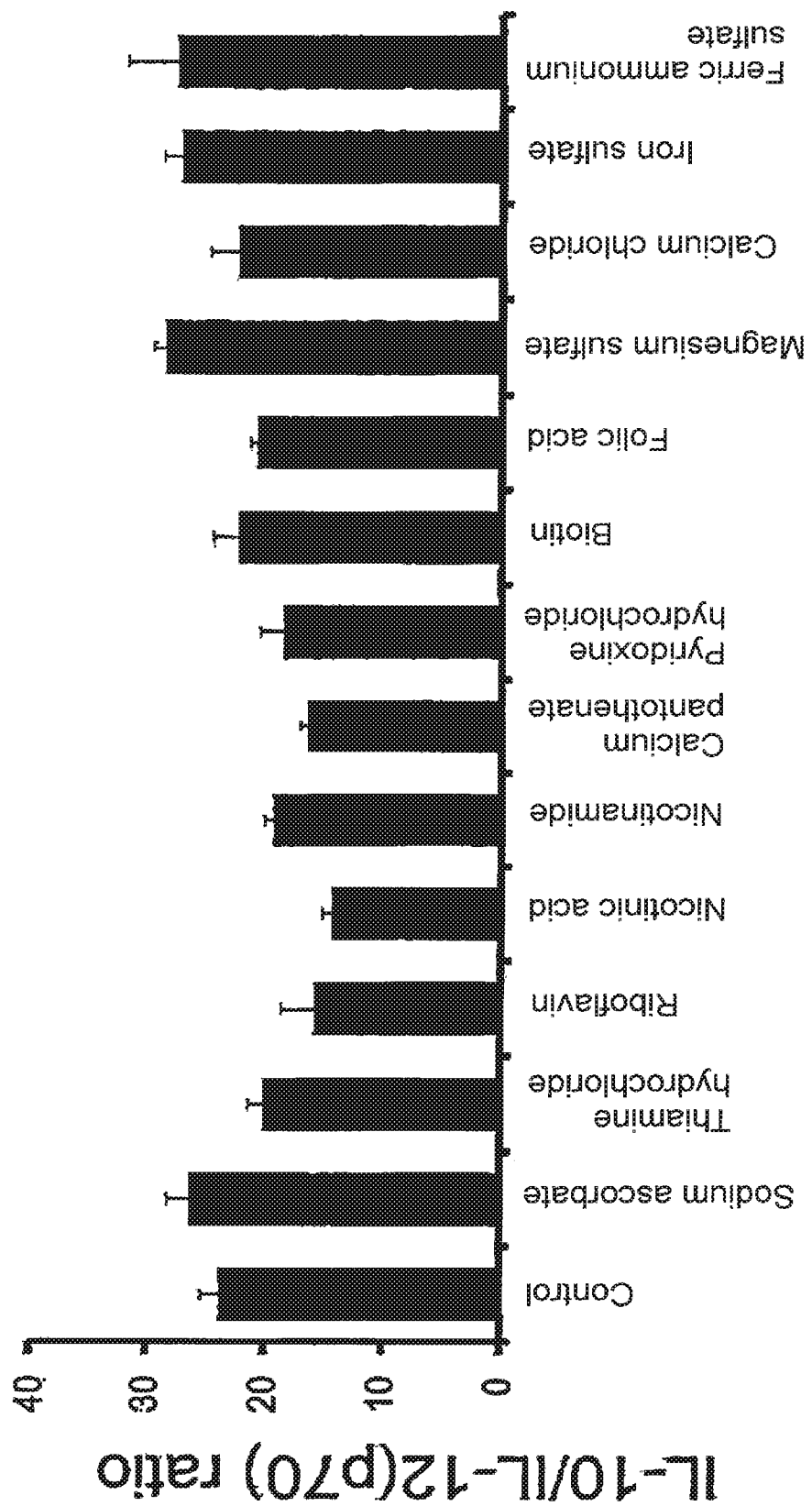
FIG. 6 is a graph for showing IL-10/IL-12 production amount ratios in the culture shown in FIG. 4.

A method of producing a culture product of *Lactobacillus plantarum* of the present invention includes culturing *Lactobacillus plantarum* using a medium containing an unsaturated fatty acid ester until a time point at or before an end of a logarithmic growth phase, to thereby obtain a culture product of *Lactobacillus plantarum*.

Any strain may be used as *Lactobacillus plantarum* (hereinafter sometimes abbreviated as *L. plantarum*).

Examples of the strain of *Lactobacillus plantarum* include OLL2712 (accession number: FERM BP-11262) and OLL2770.

In the present invention, the fatty acid ester to be used is one (i.e. unsaturated fatty acid ester) having a chemical structure having one or more double bonds (i.e. unsaturated structure) in the molecule. When a saturated fatty acid ester is used, a ratio between the production amounts of IL-10 and IL-12 (IL-10/IL-12) is decreased as compared to the case of using the unsaturated fatty acid ester.

Examples of the unsaturated fatty acid ester include: an ester formed through a reaction between a monovalent or polyvalent unsaturated fatty acid and a polyhydric alcohol; and a derivative of the ester.

Examples of the monovalent unsaturated fatty acid include a monovalent unsaturated fatty acid having 16 to 23 carbon atoms. Examples of the monovalent unsaturated fatty acid having 16 to 23 carbon atoms include oleic acid (carbon number: 16), vaccenic acid (carbon number: 16), palmitoleic acid (carbon number: 19), and nervonic acid (carbon number: 23).

Examples of the polyvalent unsaturated fatty acid include a divalent to tetravalent unsaturated fatty acid having 16 to 23 carbon atoms. Examples of the divalent to tetravalent unsaturated fatty acid having 16 to 23 carbon atoms include linoleic acid (divalent, carbon number: 16), 8,11-eicosadienoic acid (divalent, carbon number: 19), linolenic acid (trivalent, carbon number: 16), eleostearic acid (trivalent, carbon number: 16), 5,8,11-eicosatrienoic acid (trivalent, carbon number: 18), and arachidonic acid (tetravalent, carbon number: 18).

Examples of the polyhydric alcohol include polyglycerol and sorbitan. Examples of the polyglycerol include polyglycerol obtained by bonding 3 to 15 glycerols.

Examples of the polyglycerol obtained by bonding 3 to 15 glycerols include triglycerol, tetraglycerol, pentaglycerol, hexaglycerol, heptaglycerol, octaglycerol, nonaglycerol, decaglycerol, undecaglycerol, and dodecaglycerol.

Examples of the derivative of the ester formed through a reaction between a monovalent or polyvalent unsaturated fatty acid and a polyhydric alcohol include a polysorbate.

The polysorbate is a product obtained by condensing ethylene oxide with a sorbitan fatty acid formed through a reaction between a monovalent or polyvalent unsaturated fatty acid and sorbitan. In this case, the number of ethylene oxide molecules to be condensed is, for example, from 15 to 25.

In the present invention, a preferred example of the unsaturated fatty acid ester is a monooleic acid ester (e.g., one formed through a reaction between one molecule of oleic acid and one molecule of polyglycerol, sorbitan, or the polysorbate).

From the viewpoint of increasing the ratio between the production amounts of IL-10 and IL-12 (IL-10/IL-12), the concentration of the unsaturated fatty acid ester in the medium is preferably 0.001 wt % or more, more preferably 0.01 wt % or more, still more preferably 0.02 wt % or more, still more preferably 0.03 wt % or more, still more preferably 0.04 wt % or more, particularly preferably 0.05 wt % or more.

From the viewpoint of avoiding an increase in cost of the culture due to an increase in amount of the unsaturated fatty acid ester, the concentration of the unsaturated fatty acid ester in the medium is preferably 1 wt % or less, more preferably 0.5 wt % or less, still more preferably 0.3 wt % or less, still more preferably 0.1 wt % or less, particularly preferably 0.08 wt % or less.

General components used in culture of lactic acid bacteria may be used as the components of the medium other than the unsaturated fatty acid ester.

In the present invention, *Lactobacillus plantarum* is cultured until a time point at or before the end of the logarithmic growth phase. When the culture is performed until a time point beyond the end of the logarithmic growth phase, the production amount of IL-10 and the ratio between the production amounts of IL-10 and IL-12 (IL-10/IL-12) are decreased, with the result that the culture product of interest in the present invention cannot be obtained.

The end of the logarithmic growth phase is represented by, for example, the following (a) or (b).
(a) A time point at which a bacterial count during culture of the *Lactobacillus plantarum* reaches a bacterial count that is half as large as a highest attainable bacterial count
(b) A time point at which a consumption amount of a neutralizer to be used during neutral culture of the *Lactobacillus plantarum* reaches an amount that is half as large as a total consumption amount In the (a), the highest attainable bacterial count refers to the highest (i.e. maximum) bacterial count that is presumed to be attainable when the culture is continued beyond the end of the logarithmic growth phase.

In the (b), the neutral culture refers to (i.e. means) culture performed while a pH is kept to a certain range by adding a neutralizer (e.g., sodium hydroxide) to a culture broth in order to keep bacterial growth in an optimum state.

In addition, the total consumption amount of the neutralizer to be used during the neutral culture refers to (i.e. means) the total amount of the neutralizer added in the case where the neutralizer is added so that the pH may fall within the certain range from the start of the culture until the highest attainable bacterial count is obtained.

The "highest attainable bacterial count" in the (a) and the "total consumption amount" in the (b) may be determined in advance by, for example, performing culture under exactly the same conditions (e.g., the kind of the strain of *Lactobacillus plantarum*, the kinds of the unsaturated fatty acid ester and the other medium components, and the temperature during the culture) as those of an example of the production method of the present invention prior to carrying out the example.

The count of *L. plantarum* may be represented, for example, as a measured value of the turbidity of a suspension containing the culture product of *L. plantarum*. Examples of means for measuring the turbidity include a spectrophotometer.

The length of the logarithmic growth phase of *L. plantarum* varies depending on the temperature, the component composition of the medium, and the like, but is, for example, from 9 hours to 11 hours.

The culture product of *Lactobacillus plantarum* produced by the production method of the present invention may be used, for example, as an active ingredient of an anti-inflammatory agent.

The culture product can be distinguished from a culture product produced by a related-art production method (i.e. a related-art product or a conventional product) in that the ratio between the production amounts of IL-10 and IL-12 (IL-10/IL-12 production amount ratio) is larger than the ratio in the related-art product.

In the culture product produced by the production method of the present invention, the IL-10/IL-12 production amount ratio is larger preferably by 20% or more, more preferably by 25% or more, particularly preferably by 30% or more than the ratio in the case of using a medium having (i.e. including) no unsaturated fatty acid ester blended therein.

Next, a method of selecting a strain of *Lactobacillus plantarum* of the present invention is described.

The method of selecting a strain of *Lactobacillus plantarum* of the present invention (hereinafter sometimes abbreviated as selection method of the present invention) includes: culturing each of a plurality of strains of *Lactobacillus plantarum* using a medium containing an unsaturated fatty acid ester (e.g., a monooleic acid ester) until a time point at or before an end of a logarithmic growth phase, to thereby obtain a culture product of each of the strains; subjecting the obtained culture product of each of the strains to an evaluation of production-inducing activity of interleukin-10; and selecting a strain having a large degree of an anti-inflammatory action from the plurality of strains based on a result of the evaluation.

The selection method of the present invention may include subjecting the obtained culture product of each of the strains to an evaluation of production-inducing activity of interleukin-12 in addition to the evaluation of production-inducing activity of interleukin-10, in which selecting a strain having a large degree of an anti-inflammatory action from the plurality of strains is performed based on results of the evaluations.

The production-inducing activity of each of interleukin-12 and interleukin-10 may be evaluated by, for example, an immunoassay (e.g., ELISA; Enzyme-linked immuno-sorbent assay).

EXAMPLES

[1. Influence of Presence or Absence of Unsaturated Fatty Acid Ester in Medium on IL-10/IL-12 Production Amount Ratio]

*L. plantarum* OLL2712 was cultured using media having (i.e. including) vitamins, minerals, saturated fatty acid esters, or unsaturated fatty acid esters (i.e. monooleic acid esters) blended therein, and the influence of each of those components on anti-inflammatory activity was investigated.
[Experiment Method 1-1] Preparation Method for *L. plantarum* OLL2712

*L. plantarum* OLL2712 was subjected to static culture (at 37° C. for 18 hours twice) using MRS medium (manufactured by Becton, Dickinson and Company) to prepare an activated culture broth of *L. plantarum* OLL2712. Then, with the use of whey degradation medium, the activated culture broth of *L. plantarum* OLL2712 was added in an amount of 1 wt % with respect to 100 wt % of the whey degradation medium, and then subjected to static culture (at 37° C. for 9 hours) to prepare a culture broth of *L. plantarum* OLL2712.

In this case, the composition (weight basis) of the whey degradation medium contains: 6.25% of whey powder; whey protein concentrate (WPC80; protein content: 80%); 0.12% of protease; 0.50% of yeast extract; 0.50% of fish meat extract; 0.01% of manganese sulfate tetrahydrate; 0.05% (added later; details are described later) or 0% (for a control) of another auxiliary material; and 90.82% or 90.87% (for a control) of distilled water.

After that, the culture broth of *L. plantarum* OLL2712 was subjected to centrifugal treatment (8,000×g, 15 minutes) to collect bacterial cells of *L. plantarum* OLL2712. Then, thebacterial cells of *L. plantarum* OLL2712 were washed twice with physiological saline, and then the bacterial cells of *L. plantarum* OLL2712 were washed once with distilled water. After that, the resultant bacterial cells were suspended in distilled water to prepare a suspension of *L. plantarum* OLL2712. Subsequently, the suspension of *L. plantarum* OLL2712 was subjected to heat treatment (at 75° C. for 60 minutes), and then subjected to freeze-drying treatment (FD) to prepare freeze-dried bacterial cells of *L. plantarum* OLL2712.

After that, the freeze-dried bacterial cells of *L. plantarum* OLL2712 were suspended in phosphate buffered saline (PBS), and then diluted to 10 mg/mL with a medium for cell culture to prepare a dilution of *L. plantarum* OLL2712.

Here, the above-mentioned whey degradation medium (without the above-mentioned auxiliary material) was blended with an auxiliary material shown below (any one of 18 kinds in total) in an amount of 0.05 wt % to prepare 18 kinds in total of whey degradation media. After that, through treatments under conditions similar to those described above, several kinds of dilutions of *L. plantarum* OLL2712 were prepared.

[Kind of Auxiliary Material for Whey Degradation Medium]
(a) Unsaturated fatty acid ester: 4 kinds
(a-1) Decaglycerol monooleate: Sunsoft Q-17S (product name), hydrophilic, manufactured by Taiyo Kagaku Co., Ltd.
(a-2) Pentaglycerol monooleate: Sunsoft A-171E (product name), hydrophilic, manufactured by Taiyo Kagaku Co., Ltd.
(a-3) Sorbitan monooleate: Sunsoft No. 81S (product name), lipophilic, manufactured by Taiyo Kagaku Co., Ltd.
(a-4) Polyoxyethylene sorbitan monooleate: Tween 80 (product name), hydrophilic, manufactured by Wako Pure Chemical Industries, Ltd.
(b) Saturated fatty acid ester: 1 kind
(b-1) Decaglycerol monostearate: Sunsoft Q-18S (product name), amphiphilic, manufactured by Taiyo Kagaku Co., Ltd.
(c) Vitamin: 9 kinds (sodium ascorbate, thiamine hydrochloride, riboflavin, nicotinic acid, nicotinamide, calcium pantothenate, pyridoxine hydrochloride, biotin, and folic acid)
(d) Mineral: 4 kinds (magnesium sulfate, calcium chloride, iron sulfate, and ferric ammonium sulfate)

[Experiment Method 1-2] Evaluation Method for Production-Inducing Activity of IL-10 and IL-12 in Immune Cells Only undifferentiated dendritic cells were separated from the bone marrow of an 8-week-old male BALB/c mouse (Japan SLC, Inc.) using an automated magnetic cell separator (auto MACS; manufactured by Miltenyi Biotec). Then, the undifferentiated dendritic cells were cultured (at 37° C. under a $CO_2$ (5%) environment for 8 days) using RPMI medium (manufactured by Invitrogen) containing Granulocyte Macrophage Colony-Stimulating Factor (hereinafter abbreviated as GM-CSF) to be sufficiently differentiated. Thus, bone marrow-derived dendritic cells (BMDC; immune cells) were prepared.

After that, the dendritic cells (BMDC) were collected and seeded to a 48-well plate at a density of $2.5 \times 10^5$ cells/well, and then the *L. plantarum* OLL2712 cultured in any of the various whey media described above was added at a dry weight of 50 μg/mL. Then, the 48-well plate was incubated (at 37° C. under a $CO_2$ (5%) environment for 24 hours) using RPMI medium containing GM-CSF, and then the resultant culture supernatant was collected.

Then, the IL-10 concentration of the culture supernatant was measured using "Mouse IL-10 ELISA Set" (manufactured by Becton, Dickinson and Company), and the IL-12 concentration of the culture supernatant was measured using "Mouse IL-12 (p70) ELISA Set" (manufactured by Becton, Dickinson and Company). Here, for the IL-12 concentration, an activated IL-12 (p70) concentration was measured.

[Experimental Results 1] Evaluation Results of Production-inducing Activity of IL-10 and IL-12 in Immune Cells The results of the above-mentioned experiment (i.e. mean and standard deviation of four times of the experiment, and the like) are shown in Table 1 to Table 6 and FIG. 1 to FIG. 6.

In Table 1 to Table 3 (FIG. 1 to FIG. 3), the results of the case of using an unsaturated fatty acid ester (any one of 4 kinds) or a saturated fatty acid ester (1 kind; Q-18S) as an auxiliary material, and the results of the case of using no auxiliary material (Control) are shown. In Table 4 to Table 6 (FIG. 4 to FIG. 6), the results of the case of using a vitamin (any one of 9 kinds) or a mineral (anyone of 4 kinds) as an auxiliary material, and the results of the case of using no auxiliary material (Control) are shown.

TABLE 1

IL-10 production amount (unit: pg/mL)

| Kind of auxiliary material | Product name of auxiliary material | Mean | Standard deviation | Standard error |
|---|---|---|---|---|
| Not used (Control) | — | 3,122 | 316 | 158 |
| Unsaturated fatty acid ester | Q-17S | 2,880 | 158 | 79 |
| Saturated fatty acid ester | Q-18S | 3,157 | 303 | 152 |
| Unsaturated fatty acid ester | A171E | 3,128 | 95 | 48 |
| Unsaturated fatty acid ester | No. 81S | 3,514 | 114 | 57 |
| Unsaturated fatty acid ester | Tween 80 | 3,146 | 277 | 139 |

TABLE 2

IL-12 (p70) production amount (unit: pg/mL)

| Kind of auxiliary material | Product name of auxiliary material | Mean | Standard deviation | Standard error |
|---|---|---|---|---|
| Not used (Control) | — | 312 | 15 | 8 |
| Unsaturated fatty acid ester | Q-17S | 91 | 8 | 4 |
| Saturated fatty acid ester | Q-18S | 248 | 21 | 10 |
| Unsaturated fatty acid ester | A171E | 106 | 11 | 6 |
| Unsaturated fatty acid ester | No. 81S | 96 | 13 | 6 |
| Unsaturated fatty acid ester | Tween 80 | 104 | 7 | 4 |

TABLE 3

IL-10/IL-12 (p70) production amount ratio

| Kind of auxiliary material | Product name of auxiliary material | Mean | Standard deviation | Standard error |
|---|---|---|---|---|
| Not used (Control) | — | 10 | 1 | 1 |
| Unsaturated fatty acid ester | Q-17S | 32 | 2 | 1 |
| Saturated fatty acid ester | Q-18S | 13 | 1 | 0 |
| Unsaturated fatty acid ester | A171E | 30 | 3 | 1 |
| Unsaturated fatty acid ester | No. 81S | 37 | 6 | 3 |
| Unsaturated fatty acid ester | Tween 80 | 30 | 4 | 2 |

It was able to be confirmed from Table 1 (FIG. 1) that, even when *L. plantarum* OLL2712 was cultured in the whey degradation medium having a fatty acid ester (unsaturated or saturated) blended therein, the production-inducing activity of IL-10 in the immune cells was not improved as compared to the control (Control).

It was able to be confirmed from Table 2 (FIG. 2) that: when *L. plantarum* OLL2712 was cultured in the whey degradation medium having decaglycerol monostearate blended therein as a saturated fatty acid ester out of the fatty acid esters, the production-inducing activity of IL-12 in the immune cells was not significantly reduced as compared to the control (Control); and when *L. plantarum* OLL2712 was cultured in the whey degradation medium having an unsaturated fatty acid ester (any one of 4 kinds) blended therein out of the fatty acid esters, the production-inducing activity of IL-12 in the immune cells was significantly reduced as compared to the control (Control).

It was able to be confirmed from Table 3 (FIG. 3) that, when *L. plantarum* OLL2712 was cultured in the whey degradation medium having an unsaturated fatty acid ester (any one of 4 kinds) blended therein, the IL-10/IL-12 production ratio of the immune cells was significantly increased as compared to the control (Control) or the saturated fatty acid ester.

TABLE 4

IL-10 production amount (unit: pg/mL)

| Kind of auxiliary material | Mean | Standard deviation |
|---|---|---|
| Not used (Control) | 3,800 | 80 |
| Sodium ascorbate | 2,967 | 76 |
| Thiamine hydrochloride | 3,697 | 189 |
| Riboflavin | 3,683 | 244 |
| Nicotinic acid | 3,519 | 223 |
| Nicotinamide | 3,198 | 114 |
| Calcium pantothenate | 3,184 | 219 |
| Pyridoxine hydrochloride | 3,172 | 259 |
| Biotin | 3,257 | 236 |
| Folic acid | 3,091 | 97 |
| Magnesium sulfate | 3,810 | 105 |
| Calcium chloride | 3,057 | 150 |
| Iron sulfate | 2,751 | 169 |
| Ferric ammonium sulfate | 3,047 | 199 |

TABLE 5

IL-12 (p70) production amount (unit: pg/mL)

| Kind of auxiliary material | Mean | Standard deviation |
|---|---|---|
| Not used (Control) | 160 | 9 |
| Sodium ascorbate | 113 | 7 |
| Thiamine hydrochloride | 185 | 3 |
| Riboflavin | 238 | 35 |
| Nicotinic acid | 245 | 16 |
| Nicotinamide | 166 | 4 |
| Calcium pantothenate | 194 | 15 |
| Pyridoxine hydrochloride | 173 | 6 |
| Biotin | 147 | 9 |
| Folic acid | 150 | 6 |
| Magnesium sulfate | 135 | 7 |
| Calcium chloride | 139 | 14 |
| Iron sulfate | 102 | 4 |
| Ferric ammonium sulfate | 112 | 13 |

TABLE 6

IL-10/IL-12 (p70) production amount ratio

| Kind of auxiliary material | Mean | Standard deviation |
|---|---|---|
| Not used (Control) | 24 | 2 |
| Sodium ascorbate | 26 | 2 |
| Thiamine hydrochloride | 20 | 1 |
| Riboflavin | 16 | 3 |
| Nicotinic acid | 14 | 1 |
| Nicotinamide | 19 | 1 |
| Calcium pantothenate | 16 | 1 |
| Pyridoxine hydrochloride | 18 | 2 |
| Biotin | 22 | 2 |
| Folic acid | 21 | 1 |
| Magnesium sulfate | 28 | 1 |
| Calcium chloride | 22 | 2 |
| Iron sulfate | 27 | 1 |
| Ferric ammonium sulfate | 27 | 4 |

It was able to be confirmed from Table 4 (FIG. 4) that, even when *L. plantarum* OLL2712 was cultured in the whey degradation medium having a vitamin or a mineral blended therein, the production-inducing activity of IL-10 in the immune cells was not significantly changed as compared to the control (Control).

It was able to be confirmed from Table 5 (FIG. 5) that, even when *L. plantarum* OLL2712 was cultured in the whey degradation medium having a vitamin or a mineral blended therein, the production-inducing activity of IL-12 in the immune cells was not significantly changed as compared to the control (Control).

It was able to be confirmed from Table 6 (FIG. 6) that, even when *L. plantarum* OLL2712 was cultured in the whey degradation medium having a vitamin or a mineral blended therein, the IL-10/IL-12 production ratio of the immune cells was not significantly changed as compared to the control (Control).

It was able to be confirmed from the above-mentioned results that: when *L. plantarum* OLL2712 was cultured using the medium having the unsaturated fatty acid ester blended therein, the IL-10/IL-12 production ratio was remarkably increased, and hence, for example, an improvement in anti-inflammatory activity was likely to be achieved; and with a substance (i.e. saturated fatty acid ester, vitamin, or mineral) other than the unsaturated fatty acid ester, such effect (e.g., a remarkable increase in IL-10/IL-12 production ratio) was not likely to be achieved.

[2. Influence of Change in Length of Culture Period on IL-10/IL-12 Production Amount Ratio (Case of using *L. plantarum* OLL2712)]

[Experiment Method 2-1] Preparation Method for *L. plantarum* OLL2712

An activated culture broth of *L. plantarum* OLL2712 was prepared in the same manner as in the experiment method 1-1. Then, with the use of the same medium as the whey degradation medium used in the experiment method 1-1, the activated culture broth of *L. plantarum* OLL2712 was added at 4 wt %, and then subjected to stirred culture (at 33° C., under ventilation with $N_2$ at the upper surface, and at 200 rpm) while the pH was controlled to 5.8 using $K_2CO_3$ (40 wt %) as a neutralizer to prepare a high-density culture broth of *L. plantarum* OLL2712. Culture conditions for the stirred culture were investigated in advance, and set to culture conditions under which the highest bacterial cell density was obtained.

After that, freeze-dried bacterial cells of *L. plantarum* OLL2712 were prepared in the same manner as in the experiment method 1-1.

After that, the freeze-dried bacterial cells of *L. plantarum* OLL2712 were suspended in phosphate buffered saline (PBS), and then diluted to 10 mg/mL with a medium for cell culture to prepare a dilution of *L. plantarum* OLL2712.

[Experiment Method 2-2] Evaluation Method for Production-Inducing Activity of IL-10 and IL-12 in Immune Cells Production-inducing activity of IL-10 and IL-12 in immune cells was evaluated in the same manner as in the experiment method 1-2 using the whey degradation medium prepared in the experiment method 1-1 that contained decaglycerol monooleate (Sunsoft Q-17S (product name)) as an auxiliary material or contained no auxiliary material.

In this case, the production-inducing activity of IL-10 and IL-12 in the immune cells was evaluated at each of time points in the middle period of the logarithmic growth phase (4 hours after the starting point of the logarithmic growth phase), the latter period of the logarithmic growth phase (8 hours after the starting point of the logarithmic growth phase), the initial period of the stationary phase (12 hours after the starting point of the logarithmic growth phase), and the middle period of the stationary phase (16 hours after the starting point of the logarithmic growth phase).

The end of the logarithmic growth phase in this culture was a time point after a lapse of 10 hours from the starting point of the logarithmic growth phase (i.e. time point at which a bacterial count that was half as large as the highest attainable bacterial count was attained).

Figure 7:
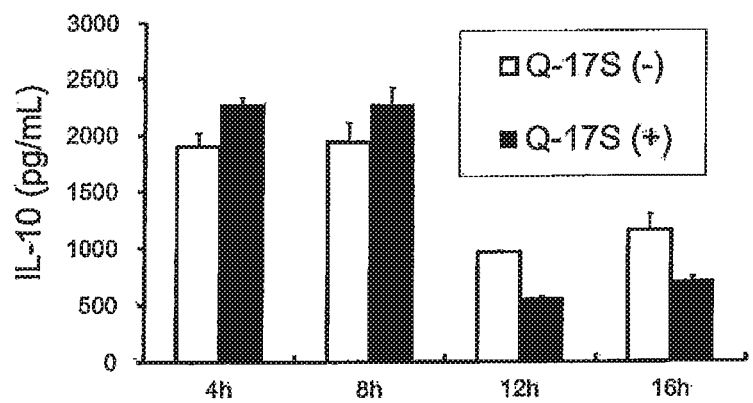
FIG. 7 is a graph for showing temporal changes in production amount of IL-10 during a culture period in cases in which *Lactobacillus plantarum* OLL2712 is cultured using a medium containing decaglycerol monooleate as one kind of unsaturated fatty acid ester (Q-17S(+)) or a medium containing no decaglycerol monooleate (Q-17S(−)).
Figure 8:
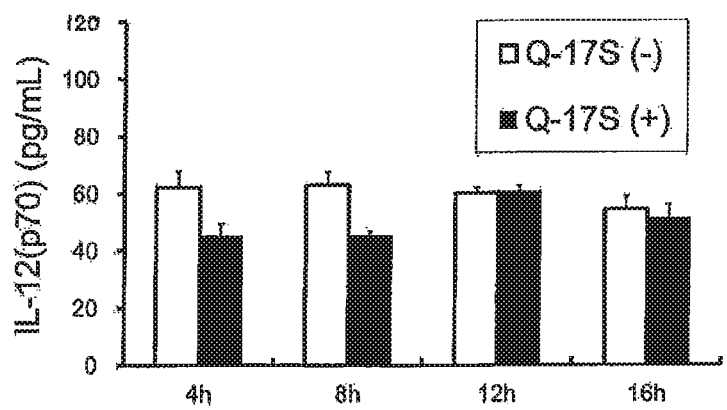
FIG. 8 is a graph for showing temporal changes in production amount of IL-12 during the culture period in the culture shown in FIG. 7.
Figure 9:
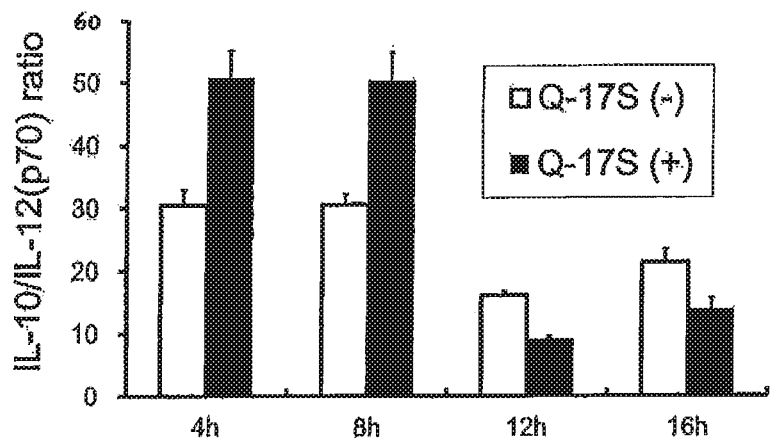
FIG. 9 is a graph for showing temporal changes in IL-10/IL-12 production amount ratio during the culture period in the culture shown in FIG. 7.

[Experimental Results 2] Evaluation Results of Production-Inducing Activity of IL-10 and IL-12 in Immune Cells The results of the above-mentioned experiment (i.e. mean and standard deviation of four times of the experiment) are shown in Table 7 to Table 9 and FIG. 7 to FIG. 9.

TABLE 7

IL-10 production amount (unit: pg/mL)

| | Representation in FIG. 7 | Elapsed time from starting point of logarithmic growth phase (hr) | Mean | Standard deviation |
|---|---|---|---|---|
| Not containing unsaturated) fatty acid ester (Q-17S) | Q-17S(−) | 4 | 1,897 | 119 |
| | | 8 | 1,938 | 171 |
| | | 12 | 965 | 13 |
| | | 16 | 1,159 | 142 |
| Containing unsaturated fatty acid ester (Q-17S) | Q-17S(+) | 4 | 2,276 | 60 |
| | | 8 | 2,276 | 145 |
| | | 12 | 557 | 17 |
| | | 16 | 709 | 29 |

TABLE 8

IL-12 (p70) production amount (unit: pg/mL)

| | Representation in FIG. 8 | Elapsed time from starting point of logarithmic growth phase (hr) | Mean | Standard deviation |
|---|---|---|---|---|
| Not containing unsaturated fatty acid ester (Q-17S) | Q-17S(−) | 4 | 62 | 5 |
| | | 8 | 63 | 4 |
| | | 12 | 60 | 2 |
| | | 16 | 54 | 5 |
| Containing unsaturated fatty acid ester (Q-17S) | Q-17S(+) | 4 | 45 | 4 |
| | | 8 | 45 | 1 |
| | | 12 | 61 | 2 |
| | | 16 | 51 | 5 |

TABLE 9

IL-10/IL-12 (p70) production amount ratio

| | Representation in FIG. 9 | Elapsed time from starting point of logarithmic growth phase (hr) | Mean | Standard deviation |
|---|---|---|---|---|
| Not containing unsaturated fatty acid ester (Q-17S) | Q-17S(−) | 4 | 31 | 2 |
| | | 8 | 31 | 2 |
| | | 12 | 16 | 1 |
| | | 16 | 21 | 2 |
| Containing unsaturated fatty acid ester (Q-17S) | Q-17S(+) | 4 | 51 | 4 |
| | | 8 | 50 | 5 |
| | | 12 | 9 | 0 |
| | | 16 | 14 | 2 |

It was able to be confirmed from Table 7 (FIG. 7) that, when *L. plantarum* OLL2712 was cultured in the whey degradation medium having the unsaturated fatty acid ester blended therein until the logarithmic growth phase (4 hours, 8 hours), the production-inducing activity of IL-10 in the immune cells was improved as compared to the case in which *L. plantarum* OLL2712 was cultured in the whey degradation medium having no unsaturated fatty acid ester blended therein until the logarithmic growth phase (4 hours, 8 hours).

In addition, it was able to be confirmed that, when *L. plantarum* OLL2712 was cultured in the whey degradation medium having the unsaturated fatty acid ester blended therein until the stationary phase (12 hours, 18 hours), the production-inducing activity of IL-10 in the immune cells was reduced as compared to the case in which *L. plantarum* OLL2712 was cultured in the whey degradation medium having no unsaturated fatty acid ester blended therein until the stationary phase (12 hours, 18 hours).

It was able to be confirmed from Table 8 (FIG. 8) that, when *L. plantarum* OLL2712 was cultured in the whey degradation medium having the unsaturated fatty acid ester blended therein until the logarithmic growth phase (4 hours, 8 hours), the production-inducing activity of IL-12 in the immune cells was reduced as compared to the case in which *L. plantarum* OLL2712 was cultured in the whey degradation medium having no unsaturated fatty acid ester blended therein until the logarithmic growth phase (4 hours, 8 hours).

In addition, it was able to be confirmed that, when *L. plantarum* OLL2712 was cultured in the whey degradation medium having the unsaturated fatty acid ester blended therein until the stationary phase (12 hours, 18 hours), the production-inducing activity of IL-12 in the immune cells was not changed as compared to the case in which *L. plantarum* OLL2712 was cultured in the whey degradation medium having no unsaturated fatty acid ester blended therein until the stationary phase (12 hours, 18 hours).

It was able to be confirmed from Table 9 (FIG. 9) that, when *L. plantarum* OLL2712 was cultured in the whey degradation medium having the unsaturated fatty acid ester blended therein until the logarithmic growth phase (4 hours, 8 hours), the IL-10/IL-12 production ratio of the immune cells was increased as compared to the case in which *L. plantarum* OLL2712 was cultured in the whey degradation medium having no unsaturated fatty acid ester blended therein until the logarithmic growth phase (4 hours, 8 hours).

In addition, it was able to be confirmed that, when *L. plantarum* OLL2712 was cultured in the whey degradation medium having the unsaturated fatty acid ester blended therein until the stationary phase (12 hours, 18 hours), the IL-10/IL-12 production ratio of the immune cells was reduced as compared to the case in which *L. plantarum* OLL2712 was cultured in the whey degradation medium having no unsaturated fatty acid ester blended therein until the stationary phase (12 hours, 18 hours).

It was able to be confirmed from the foregoing that, when *L. plantarum* OLL2712 was cultured in the whey degradation medium having the unsaturated fatty acid ester blended therein and the culture was ended at a time point in the range of the logarithmic growth phase instead of being continued until a time point in the range of the stationary phase, the IL-10/IL-12 production ratio was remarkably increased, and hence an improvement in anti-inflammatory activity was likely to be achieved.

[3. Influence of Change in Length of Culture Period on IL-10/IL-12 Production Amount Ratio (Case of using *L. plantarum* OLL2770)]

An experiment was performed in the same manner as in the section "2. Influence of Change in Length of Culture Period on IL-10/IL-12 Production Amount Ratio (Case of using *L. plantarum* OLL2712)" except that: *L. plantarum* OLL2770 was used in place of *L. plantarum* OLL2712; and the time points at which the production-inducing activity of IL-10 and IL-12 in the immune cells was measured were changed from the four time points to two time points in the middle period of the logarithmic growth phase (i.e. 5 hours after the start of the culture) and the middle period of the stationary phase (i.e. 16 hours after the start of the culture).

The end of the logarithmic growth phase in this culture was a time point after a lapse of 7 hours from the start of the culture (i.e. time point at which the consumption amount of the neutralizer reached an amount that was half as large as the total consumption amount).

Figure 10:
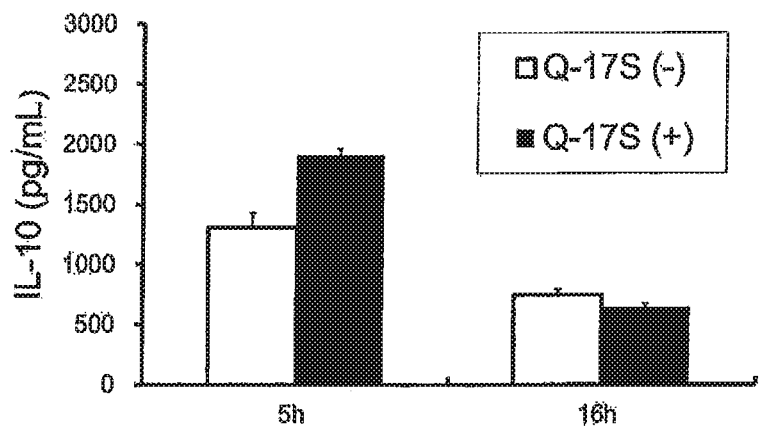
FIG. 10 is a graph for showing temporal changes in production amount of IL-10 during a culture period in cases in which *Lactobacillus plantarum* OLL2770 is cultured using a medium containing decaglycerol monooleate as one kind of unsaturated fatty acid ester (Q-17S(+)) or a medium containing no decaglycerol monooleate (Q-17S(−)).
Figure 11:
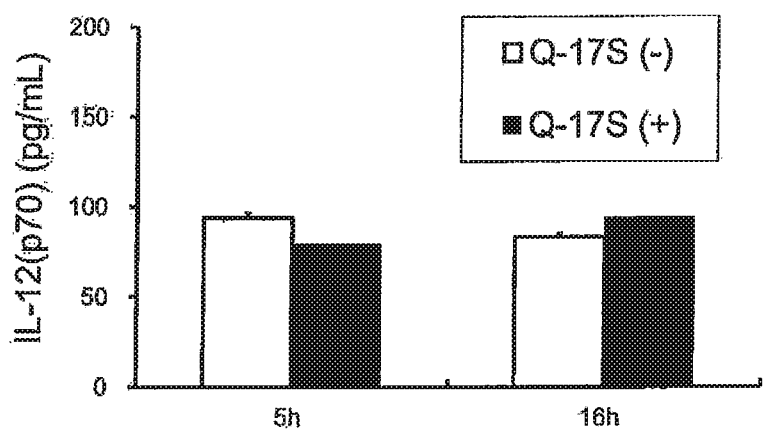
FIG. 11 is a graph for showing temporal changes in production amount of IL-12 during the culture period in the culture shown in FIG. 10.
Figure 12:
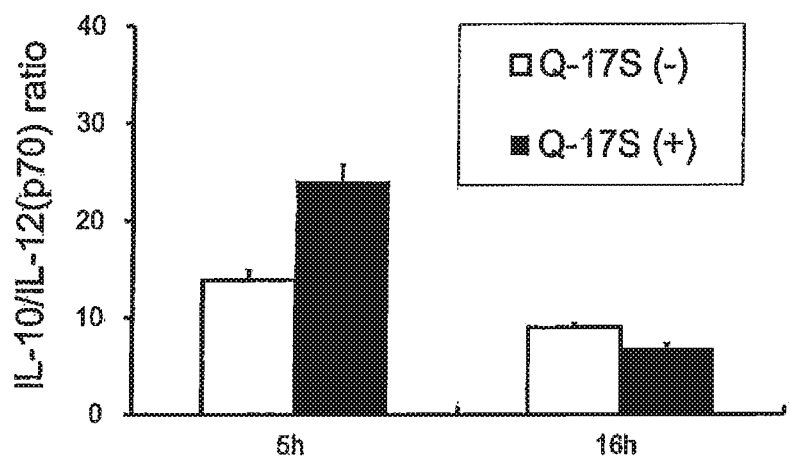
FIG. 12 is a graph for showing temporal changes in IL-10/IL-12 production amount ratio during the culture period in the culture shown in FIG. 10.

The results of the above-mentioned experiment (i.e. mean and standard deviation of four times of the experiment) are shown in Table 10 to Table 12 and FIG. 10 to FIG. 12.

TABLE 10

IL-10 production amount (unit: pg/mL)

| | Representation in FIG. 10 | Elapsed time from starting point of logarithmic growth phase (hr) | Mean | Standard deviation |
|---|---|---|---|---|
| Not containing unsaturated fatty acid ester (Q-17S) | Q-17S(−) | 5 | 1,304 | 127 |
| | | 16 | 745 | 43 |
| Containing unsaturated fatty acid ester (Q-17S) | Q-17S(+) | 5 | 1,909 | 49 |
| | | 16 | 641 | 30 |

TABLE 11

IL-12 (p70) production amount (unit: pg/mL)

| | Representation in FIG. 11 | Elapsed time from starting point of logarithmic growth phase (hr) | Mean | Standard deviation |
|---|---|---|---|---|
| Not containing unsaturated fatty acid ester (Q-17S) | Q-17S(−) | 5 | 94 | 3 |
| | | 16 | 83 | 2 |
| Containing unsaturated fatty acid ester (Q-17S) | Q-17S(+) | 5 | 80 | 4 |
| | | 16 | 94 | 8 |

TABLE 12

IL-10/IL-12 (p70) production amount ratio

| | Representation in FIG. 12 | Elapsed time from starting point of logarithmic growth phase (hr) | Mean | Standard deviation |
|---|---|---|---|---|
| Not containing unsaturated fatty acid ester (Q-17S) | Q-17S(−) | 5 | 14 | 1 |
| | | 16 | 9 | 0 |
| Containing unsaturated fatty acid ester (Q-17S) | Q-17S(+) | 5 | 24 | 2 |
| | | 16 | 7 | 0 |

It was able to be confirmed from Table 10 (FIG. 10) that, when *L. plantarum* OLL2770 was cultured in the whey degradation medium having the unsaturated fatty acid ester blended therein until the logarithmic growth phase (5 hours), the production-inducing activity of IL-10 in the immune cells was improved as compared to the case in which *L. plantarum* OLL2770 was cultured in the whey degradation medium having no unsaturated fatty acid ester blended therein until the logarithmic growth phase (5 hours).

In addition, it was able to be confirmed that, when *L. plantarum* OLL2770 was cultured in the whey degradation medium having the unsaturated fatty acid ester blended therein until the stationary phase (16 hours), the production-inducing activity of IL-10 in the immune cells was not changed as compared to the case in which *L. plantarum* OLL2770 was cultured in the whey degradation medium having no unsaturated fatty acid ester blended therein until the stationary phase (16 hours).

It was able to be confirmed from Table 11 (FIG. 11) that, when *L. plantarum* OLL2770 was cultured in the whey degradation medium having the unsaturated fatty acid ester blended therein until the logarithmic growth phase (5 hours), the production-inducing activity of IL-12 in the immune cells was significantly reduced as compared to the case in which *L. plantarum* OLL2770 was cultured in the whey degradation medium having no unsaturated fatty acid ester blended therein until the logarithmic growth phase (5 hours).

In addition, it was able to be confirmed that, when *L. plantarum* OLL2770 was cultured in the whey degradation medium having the unsaturated fatty acid ester blended therein until the stationary phase (16 hours), the production-inducing activity of IL-12 in the immune cells was not changed as compared to the case in which *L. plantarum* OLL2770 was cultured in the whey degradation medium having no unsaturated fatty acid ester blended therein until the stationary phase (16 hours).

It was able to be confirmed from Table 12 (FIG. 12) that, when *L. plantarum* OLL2770 was cultured in the whey degradation medium having the unsaturated fatty acid ester blended therein until the logarithmic growth phase (5 hours), the IL-10/IL-12 production ratio of the immune cells was increased as compared to the case in which *L. plantarum* OLL2770 was cultured in the whey degradation medium having no unsaturated fatty acid ester blended therein until the logarithmic growth phase (5 hours).

In addition, it was able to be confirmed that, when *L. plantarum* OLL2770 was cultured in the whey degradation medium having the unsaturated fatty acid ester blended therein until the stationary phase (16 hours), the IL-10/IL-12 production ratio of the immune cells was significantly reduced as compared to the case in which *L. plantarum* OLL2770 was cultured in the whey degradation medium having no unsaturated fatty acid ester blended therein until the stationary phase (16 hours).

It was able to be confirmed from the foregoing that, when *L. plantarum* OLL2770 was cultured in the whey degradation medium having the unsaturated fatty acid ester blended therein and the culture was ended at a time point in the range of the logarithmic growth phase (5 hours) instead of being continued until a time point in the range of the stationary phase (16 hours), the IL-10/IL-12 production ratio was increased, and hence an improvement in anti-inflammatory activity was likely to be achieved.

Therefore, the following was able to be confirmed to be common to *L. plantarum* without the influence of the kind of *L. plantarum*: when *L. plantarum* was cultured in the whey degradation medium having the unsaturated fatty acid ester blended therein and the culture was ended at a time point in the range of the logarithmic growth phase instead of being continued until a time point in the range of the stationary phase, the IL-10/IL-12 production ratio was increased, and hence an improvement in anti-inflammatory activity was likely to be achieved.

The invention claimed is:

1. A method of producing a culture product of *Lactobacillus plantarum*, comprising culturing *Lactobacillus plantarum* using a medium containing an effective amount of an unsaturated fatty acid ester to obtain a cultured product of *Lactobacillus plantarum* having a larger ratio of production amounts of interleukin-10 to production amounts of interleukin-12 compared to another cultured product of *Lactobacillus plantarum* obtained by culturing the *Lactobacillus plantarum* in another medium identical to the medium but without the unsaturated fatty acid ester,
wherein the culturing is continued for a time period from initiation of the culturing until an end time point, and the end time point is at or before an end of a logarithmic growth phase.

2. The method of producing a culture product of *Lactobacillus plantarum* according to claim 1, wherein the end time point of the culturing is represented by a time point at which bacterial count of the *Lactobacillus plantarum* during the logarithmic growth phase reaches a bacterial count that is half as large as a highest bacterial count attainable in the logarithmic growth phase.

3. The method of producing a culture product of *Lactobacillus plantarum* according to claim 1, wherein the end time point of the culturing is represented by a time point at which a consumption amount of a neutralizer to be used during neutral culture of the *Lactobacillus plantarum* reaches an amount that is half as large as a total consumption amount.

4. The method of producing a culture product of *Lactobacillus plantarum* according to claim 1, wherein the unsaturated fatty acid ester is an ester formed through a reaction between a monovalent or polyvalent unsaturated fatty acid and a polyhydric alcohol, or a derivative of the ester.

5. The method of producing a culture product of *Lactobacillus plantarum* according to claim 4, wherein the monovalent or polyvalent unsaturated fatty acid is a monovalent to trivalent unsaturated fatty acid having 16 to 23 carbon atoms.

6. The method of producing a culture product of *Lactobacillus plantarum* according to claim 4, wherein the unsaturated fatty acid ester is a monooleic acid ester.

7. The method of producing a culture product of *Lactobacillus plantarum* according to claim 6, wherein the unsaturated fatty acid ester is a polyglycerol fatty acid ester, a sorbitan fatty acid ester, or a polysorbate.

8. The method of producing a culture product of *Lactobacillus plantarum* according to claim 1, wherein the medium includes 0.05 wt % or more of the unsaturated fatty acid ester.

9. The method of producing a culture product of *Lactobacillus plantarum* according to claim 1, wherein the IL-10/IL-12 production amount ratio in the cultured product is larger by 20% or more compared to that obtained in the another cultured product.

10. The method of producing a culture product of *Lactobacillus plantarum* according to claim 1, wherein the unsaturated fatty acid ester is decaglycerol monooleate.

11. The method of producing a culture product of *Lactobacillus plantarum* according to claim 1, wherein the unsaturated fatty acid ester is sorbitan monooleate.

12. The method of producing a culture product of *Lactobacillus plantarum* according to claim 1, wherein the culturing is continued 9 to 11 hours from a starting point of the logarithmic growth phase.

13. A method of producing a culture product of *Lactobacillus plantarum*, comprising
culturing *Lactobacillus plantarum* using a medium containing an effective amount of an unsaturated fatty acid ester for increasing production amounts of interleukin-10 relative to production amounts of interleukin-12 in a resulting cultured product of the *Lactobacillus plantarum*,
wherein the culturing is continued for a time period from initiation of the culturing until an end time point which is at or before an end of a logarithmic growth phase.

14. The method of producing a culture product of *Lactobacillus plantarum* according to claim 13,
wherein the end time point of the culturing is represented by a time point at which bacterial count of the *Lactobacillus plantarum* during the logarithmic growth phase reaches a bacterial count that is half as large as a highest bacterial count attainable in the logarithmic growth phase.

15. The method of producing a culture product of *Lactobacillus plantarum* according to claim 13, wherein
the effective amount of the unsaturated fatty acid ester is 0.001 wt % or more, and the end time point of the culturing of the logarithmic growth phase is represented by a time point at which a consumption amount of a neutralizer to be used during neutral culture of the *Lactobacillus plantarum* reaches an amount that is half as large as a total consumption amount.

* * * * *